US009005532B2

(12) United States Patent
Baek et al.

(10) Patent No.: US 9,005,532 B2
(45) Date of Patent: Apr. 14, 2015

(54) PROCESS FOR CONTINUOUS RECOVERING (METH) ACRYLIC ACID AND APPARATUS FOR THE PROCESS

(71) Applicant: LG Chem, Ltd., Seoul (KR)

(72) Inventors: Se-Won Baek, Daejeon (KR);
Hyun-Kyu Kim, Daejeon (KR);
Dong-Hyun Cho, Daejeon (KR);
Jun-Seok Ko, Daejeon (KR)

(73) Assignee: LG Chem, Ltd., Seoul (KR)

( * ) Notice: Subject to any disclaimer, the term of this patent is extended or adjusted under 35 U.S.C. 154(b) by 5 days.

(21) Appl. No.: 14/135,190

(22) Filed: Dec. 19, 2013

(65) Prior Publication Data

US 2014/0105792 A1    Apr. 17, 2014

Related U.S. Application Data

(60) Division of application No. 13/953,599, filed on Jul. 29, 2013, now Pat. No. 8,716,525, which is a continuation of application No. PCT/KR2012/001784, filed on Mar. 12, 2012.

(30) Foreign Application Priority Data

Mar. 11, 2011    (KR) .................. 10-2011-0021818

(51) Int. Cl.
*C07B 41/08*  (2006.01)
*C07C 51/44*  (2006.01)
*C07C 51/25*  (2006.01)
*C07C 51/42*  (2006.01)
*B01D 3/00*  (2006.01)
*C07C 51/16*  (2006.01)

(52) U.S. Cl.
CPC .............. *C07C 51/44* (2013.01); *C07C 51/252* (2013.01); *C07C 51/42* (2013.01); *B01D 3/009* (2013.01); *C07C 51/16* (2013.01)

(58) Field of Classification Search
None
See application file for complete search history.

(56) References Cited

U.S. PATENT DOCUMENTS

| 4,925,981 | A | 5/1990 | Shimizu et al. | |
|---|---|---|---|---|
| 6,399,817 | B1 * | 6/2002 | Chapman et al. | 562/545 |
| 2005/0192464 | A1 | 9/2005 | Kang et al. | |
| 2005/0267313 | A1 | 12/2005 | Yada et al. | |

FOREIGN PATENT DOCUMENTS

| CN | 1309628 A | 8/2001 |
|---|---|---|
| CN | 1343195 A | 4/2002 |
| CN | 1609091 A | 4/2005 |
| CN | 1697798 A | 11/2005 |
| CN | 1914144 A | 2/2007 |
| CN | 1930108 A | 3/2007 |
| CN | 101835736 A | 9/2010 |
| JP | 58-126831 A | 7/1983 |
| JP | 2000-514076 A | 10/2000 |
| JP | 2002-514167 A | 5/2002 |
| JP | 2002-539104 A | 11/2002 |
| JP | 2002-539105 A | 11/2002 |
| JP | 2005-514417 A | 5/2005 |
| JP | 2005-336065 A | 12/2005 |
| JP | 2005-336099 A | 12/2005 |
| JP | 2007-518796 A | 7/2007 |
| JP | 2007-217401 | 8/2007 |
| JP | 2008-024716 A | 2/2008 |
| JP | 2011-500795 A | 1/2011 |
| KR | 10-2005-0016815 A | 2/2005 |
| KR | 10-0584677 B1 | 5/2006 |
| WO | 2006-14053 A1 | 2/2006 |

* cited by examiner

*Primary Examiner* — Yevegeny Valenrod
(74) *Attorney, Agent, or Firm* — McKenna Long & Aldridge LLP

(57) ABSTRACT

The present invention relates to a method and apparatus for continuous recovery of (meth)acrylic acid, and more specifically to a method of continuous recovery of (meth)acrylic acid, including: conducting gas phase oxidation of at least one compound selected from the group consisting of propane, propylene, butane, i-butylene, t-butylene, and (meth)acrolein in the presence of a catalyst to obtain a mixed gas containing (meth)acrylic acid; quenching the (meth)acrylic acid-containing mixed gas to remove high boiling point by-products in the (meth)acrylic acid-containing mixed gas; contacting the high boiling point by-product-free (meth)acrylic acid-containing mixed gas with water or an aqueous solution to obtain an aqueous solution containing (meth)acrylic acid; and purifying the aqueous solution containing (meth)acrylic acid to obtain (meth)acrylic acid.

The continuous recovery method of (meth)acrylic acid according to the present invention may significantly reduce energy consumption and continuously recover high purity (meth)acrylic acid with excellent production efficiency compared to the previous recovery methods.

7 Claims, 4 Drawing Sheets

PROCESS FOR CONTINUOUS RECOVERING (METH) ACRYLIC ACID AND APPARATUS FOR THE PROCESS

This application is a Divisional application of U.S. patent application Ser. No. 13/953,599 filed Jul. 29, 2013, which is a Continuation Bypass Application of International Patent Application No. PCT/KR2012/001784, filed Mar. 12, 2012, and claims the benefit of Korean Application No. 10-2011-0021818, filed on Mar. 11, 2011, all of which are hereby incorporated herein by reference in their entirety for all purposes as if fully set forth herein.

TECHNICAL FIELD

The present invention relates to a method of continuous recovery of (meth)acrylic acid and an apparatus used for the continuous recovery method.

BACKGROUND OF ART (Meth)acrylic acid is generally prepared by gas phase oxidation of propane, propylene, (meth)acrolein, and the like in the presence of a catalyst. For example, propane, propylene, and the like are converted to (meth)acrylic acid through (meth)acrolein by gas phase oxidation in the presence of an appropriate catalyst in a reactor, and a reaction product mixed gas including (meth)acrylic acid, non-reacted propane or propylene, (meth)acrolein, inert gas, carbon dioxide, water vapor, and various organic by-products (acetic acid, high boiling point by-products, and the like) is obtained in the back end of the reactor.

As shown in FIG. 1, the reaction product mixed gas contacts water in an absorption tower (102), soluble gas is obtained as a (meth)acrylic acid aqueous solution together with water, and non-soluble gas is discharged to the top of the absorption tower and recycled to the gas phase oxidation reactor, or converted to harmless gas through an incinerator and discharged.

Also, the (meth)acrylic acid aqueous solution is supplied to a distillation tower (105), which is a water separation tower, and high concentration (meth)acrylic acid is obtained at the bottom of the distillation tower. In the distillation tower (105), azeotropic distillation is mainly used, wherein water is separated using a solvent that forms an azeotrope with water. Herein, the operation method of a separation column of the back end, the treatment method of separated water, and the like are significantly varied according to the selection of an azeotropic solvent.

For example, if a hydrophilic azeotropic solvent such as methylisobutylketone (MIBK) is used as the azeotropic solvent of the distillation tower (105), azeotropic removal of acetic acid may be difficult, only water may be removed in the distillation tower (105), and (meth)acrylic acid containing a large amount of acetic acid is recovered from the bottom of the distillation tower (105). Thus, to remove acetic acid, a low boiling point separation tower (107) and an acetic acid separation tower (109) are required, and finally, after passing through a high boiling point separation tower (108), crude (meth)acrylic acid is recovered.

For another example, as shown in FIG. 2, if a hydrophobic azeotropic solvent such as toluene is used as the azeotropic solvent of the distillation tower (105), main by-products of acetic acid form an azeotrope together with water and are recovered at one time. Thus, the purification steps in the low boiling point separation tower (107) and acetic acid separation tower (109) in FIG. 1 may be dispensed with, nearly pure (meth)acrylic acid is obtained together with high boiling point by-products at the bottom of the distillation tower (105), and subsequently, after passing through the high boiling point separation tower (108) for removing the high boiling point by-products, crude (meth)acrylic acid may be recovered.

Particularly, in Korean Published Application No. 2009-0041355, the inventors have suggested a method of reducing waste water amount and effectively inhibiting inflow of organics in a reactor, by circulating acetic acid-containing waste water that is generated from the top of the distillation tower(105) if a hydrophobic azeotropic solvent is used to the (meth)acrylic acid absorption tower(102) and reusing it.

However, although the method may achieve the effect of simplifying subsequent purification steps by using a hydrophobic azeotropic solvent, high temperature (meth)acrylic acid-containing gas should be still cooled, absorbed, and redistilled, and in the subsequent purification step, a high boiling point distillation tower (108) should be operated. Thereby, the energy consumption amount of the overall process increases, and problems such as polymer production in the distillation tower (105) due to the high boiling point by-products still exist.

DETAILED DESCRIPTION OF THE INVENTION

Technical Problem

The present invention provides a method that may reduce energy consumption amount in the total process, and operate a distillation tower more stably and thus continuously recover high purity (meth)acrylic acid with excellent production efficiency, compared to previous recovery methods.

The present invention also provides an apparatus for continuous recovery of (meth)acrylic acid.

Technical Solution

According to the present invention,
a method of continuous recovery of (meth)acrylic acid is provided, including:
conducting gas phase oxidation of at least one compound selected from the group consisting of propane, propylene, butane, i-butylene, t-butylene, and (meth)acrolein in the presence of a catalyst to obtain a mixed gas containing (meth)acrylic acid;
quenching the (meth)acrylic acid-containing mixed gas to remove high boiling point by-products in the (meth)acrylic acid-containing mixed gas;
contacting the high boiling point by-product-free (meth)acrylic acid-containing mixed gas with water or an aqueous solution to obtain an aqueous solution containing (meth)acrylic acid; and
purifying the (meth)acrylic acid-containing aqueous solution to obtain (meth)acrylic acid.

The (meth)acrylic acid-containing mixed gas obtained by the gas phase oxidation may have a temperature of 150 to 250° C.

The step of quenching the (meth)acrylic acid-containing mixed gas may be conducted in a quench tower at a pressure of 1 to 1.5 bar and an upper temperature of 70 to 150° C., wherein the high boiling point by-products may be discharged to the bottom of the quench tower, and the high boiling point by-product-free (meth)acrylic acid-containing mixed gas may be discharged to the top of the quench tower.

The (meth)acrylic acid-containing mixed gas may be supplied to the quench tower and quenched by recycled liquid at the bottom of the quench tower and the (meth)acrylic acid-containing aqueous solution.

The step of contacting the high boiling point by-product-free (meth)acrylic acid-containing mixed gas with water or an aqueous solution may be conducted in a (meth)acrylic acid absorption tower at a pressure of 1 to 1.5 bar and an upper temperature of 50 to 70° C., wherein the (meth)acrylic acid-containing aqueous solution may be discharged to the bottom of the (meth)acrylic acid absorption tower, and a (meth)acrylic acid-stripped non-condensable gas may be discharged to the top of the (meth)acrylic acid absorption tower.

In the above step, the (meth)acrylic acid-containing aqueous solution may include 40 to 90 wt % of (meth)acrylic acid.

Further, 5 to 80 wt % of the (meth)acrylic acid-containing aqueous solution discharged to the bottom of the (meth)acrylic acid absorption tower may be supplied to the top of the quench tower, and the remainder may be supplied in the purifying step.

The method may further include a step of contacting the non-condensable gas discharged to the top of the (meth)acrylic acid absorption tower with water to recover acetic acid included in the non-condensable gas.

The step of contacting the non-condensable gas with water may be conducted in an acetic acid absorption tower at a pressure of 1 to 1.5 bar and an upper temperature of 50 to 70° C., wherein the acetic acid aqueous solution discharged to the bottom of the acetic acid absorption tower may be recycled to the top of the (meth)acrylic acid absorption tower, and a substance discharged to the top of the acetic acid absorption tower may be recycled to the gas phase oxidation step.

The step of purifying the (meth)acrylic acid-containing aqueous solution may be conducted in a distillation tower supplied with a hydrophobic azeotropic solvent, wherein a discharged liquid including (meth)acrylic acid may be recovered from the bottom of the distillation tower, and a discharged liquid including the azeotropic solvent, water, and acetic acid may be recovered from the bottom of the distillation tower.

The hydrophobic azeotropic solvent may be at least one selected from the group consisting of benzene, toluene, xylene, N-heptane, cycloheptane, cycloheptene, 1-heptene, ethyl-benzene, methyl-cyclohexane, N-butyl acetate, isobutyl acetate, isobutyl acrylate, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

Acetic acid may be included in the water layer of the discharged liquid including the azeotropic solvent, water, and acetic acid, recovered from the top of the distillation tower, in a concentration of 1 to 50 wt %.

The discharged liquid including the azeotropic solvent, water, and acetic acid, recovered from the top of the distillation tower, may be supplied to a solvent decanter to separate into an azeotropic solvent layer and an acetic acid aqueous solution layer, the azeotropic solvent layer may be recycled to the top of the distillation tower, and the acetic acid aqueous solution layer may be recycled to the step of contacting the high boiling point by-product-free (meth)acrylic acid-containing mixed gas with water or an aqueous solution.

The liquid discharged from the bottom of the distillation tower may include less than 1 wt % of water and acetic acid, and less than 500 ppm of the azeotropic solvent.

The method of continuous recovery of (meth)acrylic acid according to the present invention may further include the step of crystallizing the liquid discharged from the bottom of the distillation tower.

The method may further include the step of recovering (meth)acrylic acid by thermal decomposition of high boiling point by-products respectively recovered in the step of quenching the (meth)acrylic acid-containing mixed gas and in the step of crystallizing the liquid discharged from the bottom of the distillation tower.

The (meth)acrylic acid recovered by the thermal decomposition of high boiling point by-products may be recycled to the step of quenching the (meth)acrylic acid-containing mixed gas.

Meanwhile, according to the present invention,
an apparatus for continuous recovery of (meth)acrylic acid is provided, including:

a gas phase oxidation reactor for conducting gas phase oxidation of at least one compound selected from the group consisting of propane, propylene, butane, i-butylene, t-butylene, and (meth)acrolein in the presence of a catalyst, to prepare a mixed gas containing (meth)acrylic acid;

a quench tower for quenching the (meth)acrylic acid-containing mixed gas supplied from the gas phase oxidation reactor to remove high boiling point by-products in the (meth)acrylic acid-containing mixed gas;

a (meth)acrylic acid absorption tower for contacting the high boiling point by-product-free (meth)acrylic acid-containing mixed gas with water or an aqueous solution to obtain an aqueous solution containing (meth)acrylic acid; and a distillation tower for purifying the (meth)acrylic-containing aqueous solution supplied from the (meth)acrylic acid absorption tower, to obtain (meth)acrylic acid.

Herein, the quench tower may be connected to and integrated with the bottom of the (meth)acrylic acid absorption tower.

Advantageous Effects

The continuous recovery method of (meth)acrylic acid according to the present invention may significantly reduce energy consumption and continuously recover high purity (meth)acrylic acid with excellent production efficiency compared to the previous recovery methods.

DETAILED DESCRIPTION OF THE EMBODIMENTS

Figure 1:
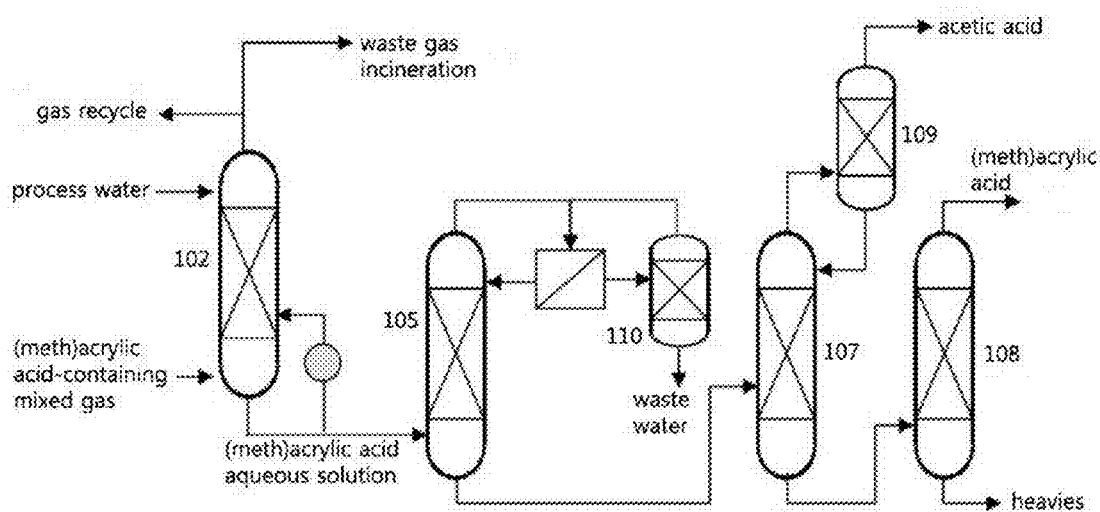
FIG. 1 and FIG. 2 are process diagrams schematically showing the existing continuous recovery methods of (meth)acrylic acid.

Unless otherwise described, terms used herein are defined as follows.

First, '(meth)acrylic acid' generally refers to acrylic acid and/or methacrylic acid.

Further, '(meth)acrylic acid-containing mixed gas' generally refers to a mixed gas that may be produced when (meth)acrylic acid is prepared by gas phase oxidation. Namely, according to one embodiment of the invention, the (meth)acrylic acid-containing mixed gas may be obtained by gas phase oxidation of at least one compound selected from the group consisting of propane, propylene, butane, i-butylene, t-butylene and (meth)acrolein ('raw material compound') in the presence of a catalyst. Herein, the (meth)acrylic acid-containing mixed gas may include (meth)acrylic acid, non-reacted raw material compounds, (meth)acrolein, inert gas, carbon monoxide, carbon dioxide, water vapor, various organic by-products (acetic acid, high boiling point by-products, and the like), and the like.

Also, 'high boiling point by-products' (heavies) refer to by-products that may be produced in preparation and recovery processes of (meth)acrylic acid, and generally refer to materials having higher molecular weight than (meth)acrylic acid. Namely, the high boiling point by-products include high molecular weight materials produced in the gas phase oxidation for preparing (meth)acrylic acid; and include (meth)acrylic acid polymers (dimers, oligomers, and the like) that may be produced in the purification process of the (meth)acrylic acid-containing aqueous solution, polymerization inhibitors that may be used in the purification process, and the like.

Hereinafter, referring to attached drawings, a method and an apparatus for continuous recovery of (meth)acrylic acid according to embodiments of the invention will be explained.

The present invention is based on the discovery that if a step for removing high boiling point by-products is operated before passing a (meth)acrylic acid absorption tower in the early stage of the process, the high boiling point by-products may be removed by process energy without supplying additional energy, and since the high boiling point by-products may be removed beforehand, total process efficiency may be improved.

According to one embodiment of the invention, a method of continuous recovery of (meth)acrylic acid is provided, including:

conducting gas phase oxidation of at least one compound selected from the group consisting of propane, propylene, butane, i-butylene, t-butylene, and (meth)acrolein in the presence of a catalyst, to obtain a mixed gas containing (meth)acrylic acid;

quenching the (meth)acrylic acid-containing mixed gas to remove high boiling point by-products in the (meth)acrylic acid-containing mixed gas;

contacting the high boiling point by-product-free (meth)acrylic acid-containing mixed gas with water or an aqueous solution, to obtain an aqueous solution containing (meth)acrylic acid; and purifying the (meth)acrylic acid-containing aqueous solution to obtain (meth)acrylic acid.

Hereinafter, referring to FIG. 3 and FIG. 4, each step that may be included in the recovery method according to the present invention will be explained in detail.

First, the method of continuous recovery of (meth)acrylic acid according to one embodiment of the invention includes a step of obtaining (meth)acrylic acid-containing mixed gas by gas phase oxidation.

The (meth)acrylic acid-containing mixed gas may be obtained by gas phase oxidation of at least one compound selected from the group consisting of propane, propylene, butane, i-butylene, t-butylene, and (meth)acrolein (raw material compound) in the presence of a catalyst, as defined above.

Herein, the gas phase oxidation may progress under common conditions in a common gas phase oxidation reactor. Also, in the gas phase oxidation, a commonly used catalyst may be used as the catalyst, and preferably, those disclosed in Korean Registered Patent No. 0349602 and No. 037818 and the like may be used, but are not limited thereto.

The (meth)acrylic acid-containing mixed gas produced by gas phase oxidation may include non-reacted raw material compounds, intermediate product (meth)acrolein, inert gas, carbon dioxide, water vapor, and various organic by-products (acetic acid, high boiling point by-products, and the like), as well as the end product (meth)acrylic acid.

Meanwhile, the continuous recovery method of (meth)acrylic acid according to one embodiment of the invention includes a step of quenching the (meth)acrylic acid-containing mixed gas to remove high boiling point by-products in the (meth)acrylic acid-containing mixed gas.

In the above step, high boiling point by-products are preferentially removed in the (meth)acrylic acid-containing mixed gas obtained in the preceding step.

Figure 2:
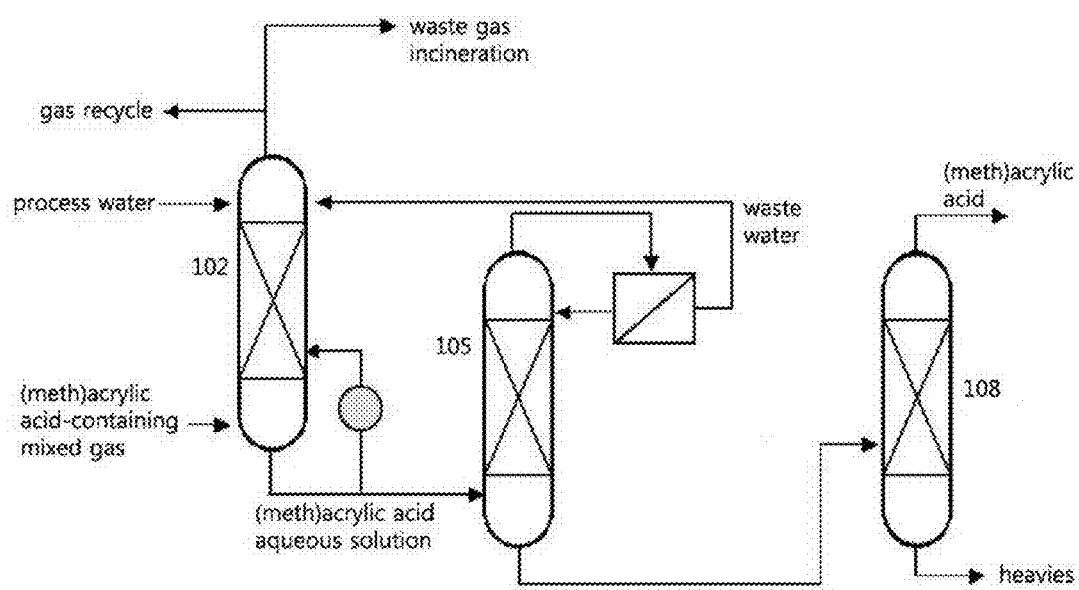

Specifically, high boiling point by-products are included in the (meth)acrylic acid-containing mixed gas, and according to previous recovery methods, as shown in FIG. 1 and FIG. 2, the (meth)acrylic acid-containing mixed gas is supplied to an acrylic acid absorption tower (102) and passed through a distillation tower (105), and the like. Thus, high boiling point by-products are included during the whole process, and are thus attached to the wall surfaces of various reactors or pipes, thereby lowering energy efficiency and inducing polymerization of (meth)acrylic acid in the distillation tower (105) to deteriorate overall production efficiency.

Therefore, the present invention is to maximize energy efficiency by removing high boiling point by-products in the (meth)acrylic acid-containing mixed gas in advance, and solve the problems of the previous recovery method.

According to one embodiment of the invention, the step of removing high boiling point by-products in the (meth)acrylic acid-containing mixed gas may be conducted by quenching the (meth)acrylic acid-containing mixed gas, which is preferably conducted in a quench tower (101).

Specifically, the (meth)acrylic acid-containing mixed gas is supplied to the bottom of the quench tower(101), wherein the temperature of the (meth)acrylic acid-containing mixed gas supplied to the quench tower(101) may be 150 to 250° C., preferably 150 to 200° C.

Particularly, according to one embodiment of the invention, the (meth)acrylic acid-containing mixed gas may be supplied to the quench tower (101), and quenched by recycled liquid at the bottom of the quench tower (101) and a (meth)acrylic acid-containing aqueous solution discharged from the bottom of the (meth)acrylic acid absorption tower (102) as described below. Thereby, the high boiling point by-products may be removed by process energy without supplying additional energy, thus improving energy efficiency.

Herein, the quench tower (101) may be operated at a pressure of 1 to 1.5 bar, preferably 1 to 1.3 bar considering condensation conditions of high boiling point by-products, and the like; and the upper temperature of the quench tower (101) may be controlled to 30 to 150° C., preferably 50 to 120° C., and more preferably 50 to 100° C.

By the quenching, high boiling point by-products are discharged to the bottom the quench tower (101), and the high boiling point by-product-free (meth)acrylic acid-containing mixed gas is discharged to the top of the quench tower (101).

Herein, the high boiling point by-products discharged to the bottom of the quench tower (101) may be thermally decomposed in a separate cracker, which will be described below.

Further, the high boiling point by-product-free (meth)acrylic acid-containing mixed gas discharged to the top of the quench tower (101) is continuously supplied to a step of obtaining a (meth)acrylic acid-containing aqueous solution.

Meanwhile, the continuous recovery method of (meth)acrylic acid according to one embodiment of the invention includes a step of contacting the high boiling point by-product-free (meth)acrylic acid-containing mixed gas with water or an aqueous solution, to obtain an aqueous solution containing (meth)acrylic acid.

According to one embodiment of the invention, the step of obtaining the (meth)acrylic acid-containing aqueous solution may be conducted in a (meth)acrylic acid absorption tower (102).

Specifically, the high boiling point by-product-free (meth)acrylic acid-containing mixed gas is supplied to the bottom of the (meth)acrylic acid absorption tower (102). Further, process water or an aqueous solution for absorbing (meth)acrylic acid is supplied to the top of the (meth)acrylic acid absorption tower (102), wherein the process water may be separately introduced, and preferably it may include an aqueous solution discharged from the bottom of an acetic acid absorption tower (103) as described below, and/or an aqueous solution separated in a distillation tower (105) as described below.

Specifically, the aqueous solution contacting the high boiling point by-product-free (meth)acrylic acid-containing mixed gas contains a lower concentration of (meth)acrylic acid than the (meth)acrylic acid-containing aqueous solution, and it may be an aqueous solution discharged from the bottom part of the acetic acid absorption tower (103), an aqueous solution separated in the distillation tower (105), or a mixture thereof. Herein, the aqueous solution separated in the distillation tower (105) refers to an aqueous solution that is recycled to the (meth)acrylic acid absorption tower (102) after obtaining (meth)acrylic acid by purifying the (meth)acrylic acid-containing aqueous solution, which process will be explained below. Since the aqueous solution contacting the high boiling point by-product-free (meth)acrylic acid-containing mixed gas may be supplied from the acetic acid absorption tower (103) and/or distillation tower (105), it may further include acetic acid.

Meanwhile, the (meth)acrylic acid absorption tower (102) may be operated at a pressure of 1 to 1.5 bar, and preferably 1 to 1.3 bar considering condensation conditions of (meth)acrylic acid and moisture content conditions according to saturated water vapor pressure, and the like; and the upper temperature of the (meth)acrylic acid absorption tower (102) may be controlled to 30 to 150° C., preferably 50 to 100° C., and more preferably 50 to 80° C.

Through the above process, a (meth)acrylic acid-containing aqueous solution is discharged to the bottom of the (meth)acrylic acid absorption tower (102), and (meth)acrylic acid-stripped non-condensable gas is discharged to the top of the (meth)acrylic acid absorption tower (102).

Herein, a part of the non-condensable gas discharged to the top of the (meth)acrylic acid absorption tower (102) may be supplied to a waste gas incinerator, and the remainder may be supplied to a step of recovering acetic acid.

Namely, according to one embodiment of the invention, the method may further include a step of contacting the non-condensable gas discharged to the top of the (meth)acrylic acid absorption tower (102) with water to recover acetic acid included in the non-condensable gas.

The step of contacting the non-condensable gas with water may be conducted in an acetic acid absorption tower (103); for an effective acetic acid absorption process, the acetic acid absorption tower (103) may be operated at a pressure of 1 to 1.5 bar, preferably 1 to 1.3 bar; and the upper temperature of the acetic acid absorption tower (103) may be controlled to 30 to 150° C., preferably 50 to 100° C., and more preferably 50 to 80° C. In addition, specific operation conditions of the acetic acid absorption tower (103) may be as described in Korean Published Application No. 2009-0041355 of the applicant.

Process water for recovering acetic acid included in the non-condensable gas is introduced into the top of the acetic acid absorption tower (103), an acetic acid aqueous solution is discharged to the bottom of the acetic acid absorption tower (103), and the acetic acid aqueous solution may be supplied to the top of the (meth)acrylic acid absorption tower(102) to use as process water for absorbing (meth)acrylic acid. Also, acetic acid-stripped gas may be discharged to the top of the acetic acid absorption tower (103) and recycled in the above-explained gas phase oxidation step.

Meanwhile, a (meth)acrylic acid-containing aqueous solution is discharged to the bottom of the (meth)acrylic acid absorption tower(102), wherein it is appropriate that the (meth)acrylic acid-containing may include 40 to 90 wt %, preferably 50 to 90 wt %, and more preferably 50 to 80 wt % of (meth)acrylic acid in terms of process efficiency.

By supplying a part of the (meth)acrylic acid-containing aqueous solution discharged to the bottom of the (meth)acrylic acid absorption tower (102) to the top of the above-explained quench tower (101), it may be used for quenching the (meth)acrylic acid-containing mixed gas. Thereby, high boiling point by-products may be effectively removed without supplying separate energy to the above-explained quenching step, thus improving energy efficiency. Considering overall process efficiency, the (meth)acrylic acid-containing aqueous solution supplied to the top of the quench tower (101) may be controlled to 5 to 80 wt %, preferably 10 to 70 wt %, and more preferably 10 to 50 wt % of the (meth)acrylic acid-containing aqueous solution discharged to the bottom of the (meth)acrylic acid absorption tower (102).

A part of the (meth)acrylic acid-containing aqueous solution discharged to the bottom of the (meth)acrylic acid absorption tower (102) may be recycled to the (meth)acrylic acid absorption tower (102) through a heat exchanger to assist in the absorption process, and the remainder may be supplied to the subsequent purification step via a stripping tower (not shown).

The continuous recovery method of (meth)acrylic acid according to one embodiment of the invention includes a step of purifying the (meth)acrylic acid-containing aqueous solution to obtain (meth)acrylic acid.

The purification of the (meth)acrylic acid-containing aqueous solution may be conducted in a distillation tower (105) supplied with a hydrophobic azeotropic solvent, discharged liquid including (meth)acrylic acid may be recovered from the bottom of the distillation tower, and discharged liquid including the azeotropic solvent, water, and acetic acid may be recovered from the top of the distillation tower.

By using a hydrophobic solvent as the azeotropic solvent, water and acetic acid included in the (meth)acrylic acid-containing aqueous solution may be simultaneously recovered from the top of the distillation tower (105).

As the hydrophobic solvent, hydrocarbon-based solvents which form an azeotrope with water and acetic acid and do not form an azeotrope with (meth)acrylic acid may be used without limitation; preferably, it may be hydrocarbons with a boiling point of 10 to 120° C.; more preferably, it may be at least one selected from the group consisting of benzene, toluene, xylene, N-heptane, cycloheptane, cycloheptene, 1-heptene, ethyl-benzene, methyl-cyclohexane, N-butyl acetate, isobutyl acetate, isobutyl acrylate, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

Discharged liquid including the azeotropic solvent, water, and acetic acid is recovered from the top of the distillation tower (105), and the concentration of the acetic acid included in the water layer of the liquid discharged from the top may be varied according to the kind of the azeotropic solvent and reflux ratio of the column, and the like. According to the present invention, the concentration of acetic acid included in the water layer of the liquid discharged from the top may be 1 to 50 wt %, preferably 3 to 45 wt %, and more preferably 5 to 40 wt %, considering loss of (meth)acrylic acid, and the like.

Discharged liquid including an azeotropic solvent, water, and acetic acid recovered from the top of the distillation tower (105) may be supplied to a solvent decanter 110 to separate into an azeotropic solvent layer and an acetic acid aqueous solution layer, and then the azeotropic solvent layer may be recycled to the top of the distillation tower (105) and the acetic acid aqueous solution layer may be recycled to the (meth)acrylic acid absorption tower (102).

From the bottom of the distillation tower (105), (meth)acrylic acid-containing discharged liquid almost free of water, acetic acid, and an azeotropic solvent is recovered, and it may be used as crude (meth)acrylic acid.

Water, acetic acid, and the azeotropic solvent may be partially included in the liquid discharged from the bottom of the distillation tower (105), and it is preferable that the liquid discharged from the bottom may respectively include less than 1 wt % of water and acetic acid, and less than 500 ppm of the azeotropic solvent, so as to be appropriately used as crude (meth)acrylic acid.

Meanwhile, (meth)acrylic acid may be polymerized during the purification of the (meth)acrylic acid-containing aqueous solution, thereby producing a (meth)acrylic acid polymer such as a dimer or oligomer, and the like. As such, to minimize polymerization of (meth)acrylic acid, a polymerization inhibitor may be added to the distillation tower (105), wherein those commonly used in the art may be used as the polymerization inhibitor without limitation.

The high boiling point by-products including the (meth)acrylic acid polymer, the polymerization inhibitor, and the like may be included in the liquid discharged from the bottom of the distillation tower (105) and recovered, and a step for selectively recovering (meth)acrylic acid from the liquid discharged from the bottom of the distillation tower (105) may be further conducted.

That is, according to one embodiment of the invention, the method may further include a step of crystallizing liquid discharged from the bottom of the distillation tower (105).

The crystallization step may be conducted in a crystallizer (106), wherein the crystallizer may consist of two or more stages. For example, in a first crystallizer (106), high boiling point by-products including a (meth)acrylic acid polymer, a polymerization inhibitor, and the like included in the liquid discharged from the bottom of the distillation tower (105) are removed, thereby selectively obtaining crude (meth)acrylic acid (CAA). In a connected second crystallizer (106'), the crude (meth)acrylic acid (CAA) is highly crystallized, thus obtaining high purity (meth)acrylic acid (HP AA).

As the crystallizers (106 and 106') used in the crystallization step, a static device, a dynamic device, or a combined device commonly used in the art may be used, but are not limited thereto.

Meanwhile, in the high boiling point by-products including the (meth)acrylic acid polymer, the polymerization inhibitor, and the like separated in the first crystallizer (106), a significant amount of the (meth)acrylic acid and the (meth)acrylic acid polymer may be included.

Thus, the recovery method of the present invention may further include a step of recovering (meth)acrylic acid by thermal decomposition of the high boiling point by-products recovered in the step of recystallizing liquid discharged from the bottom of the distillation tower (105) and the high boiling point by-products recovered in the above-explained quench tower (101).

For thermal decomposition of the high boiling point by-products, an apparatus including an evaporator/recovery machine, a cracker, and the like may be used, preferably as described in Korean Registered Patent No. 0714631 of the applicant.

Specifically, the thermal decomposition of the high boiling point by-products may include introducing the high boiling point by-products into a (meth)acrylic acid recovery device wherein a (meth)acrylic acid distillator and a (meth)acrylic acid polymer cracker are integrated, decomposing the (meth)acrylic acid polymer at the bottom of the (meth)acrylic acid recovery device under reduced pressure, and recovering the (meth)acrylic acid from the top of the (meth)acrylic acid recovery device by distillation.

The (meth)acrylic acid that can be recovered from the high boiling point by-products by the above method may be recycled to the above-explained quench tower (102).

Figure 3:
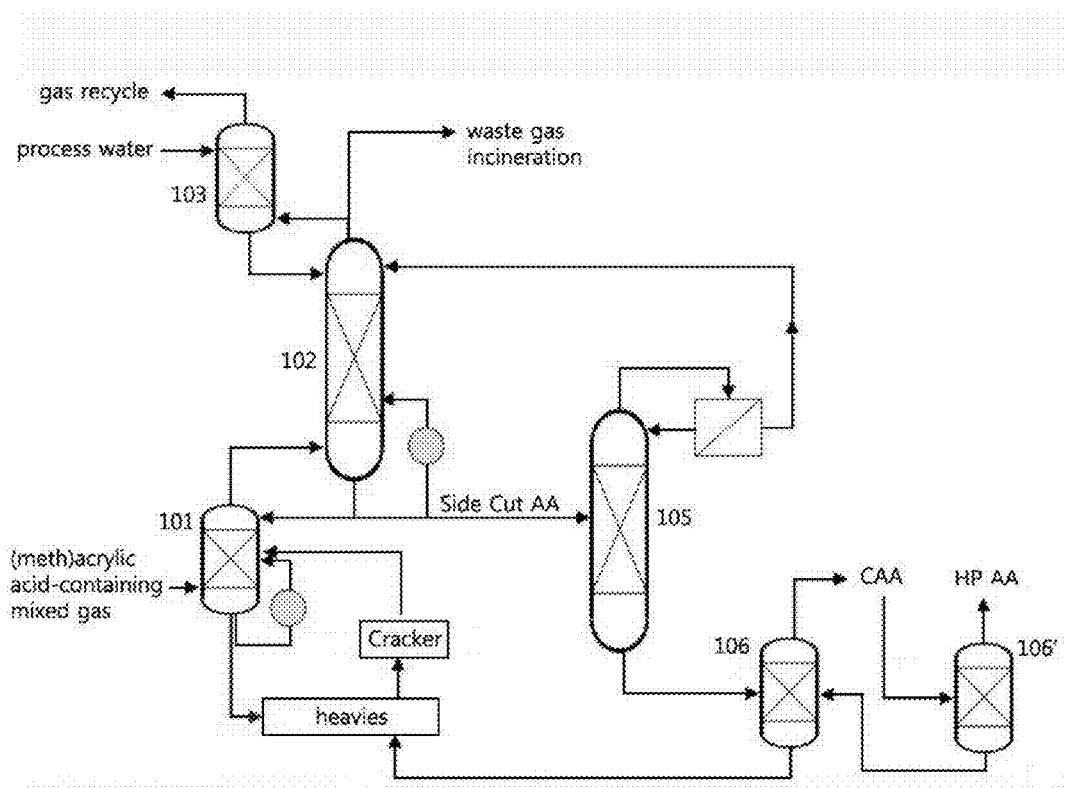
FIG. 3 and FIG. 4 are process diagrams schematically showing the continuous recovery method of (meth)acrylic acid according to embodiments of the invention.
Figure 4:
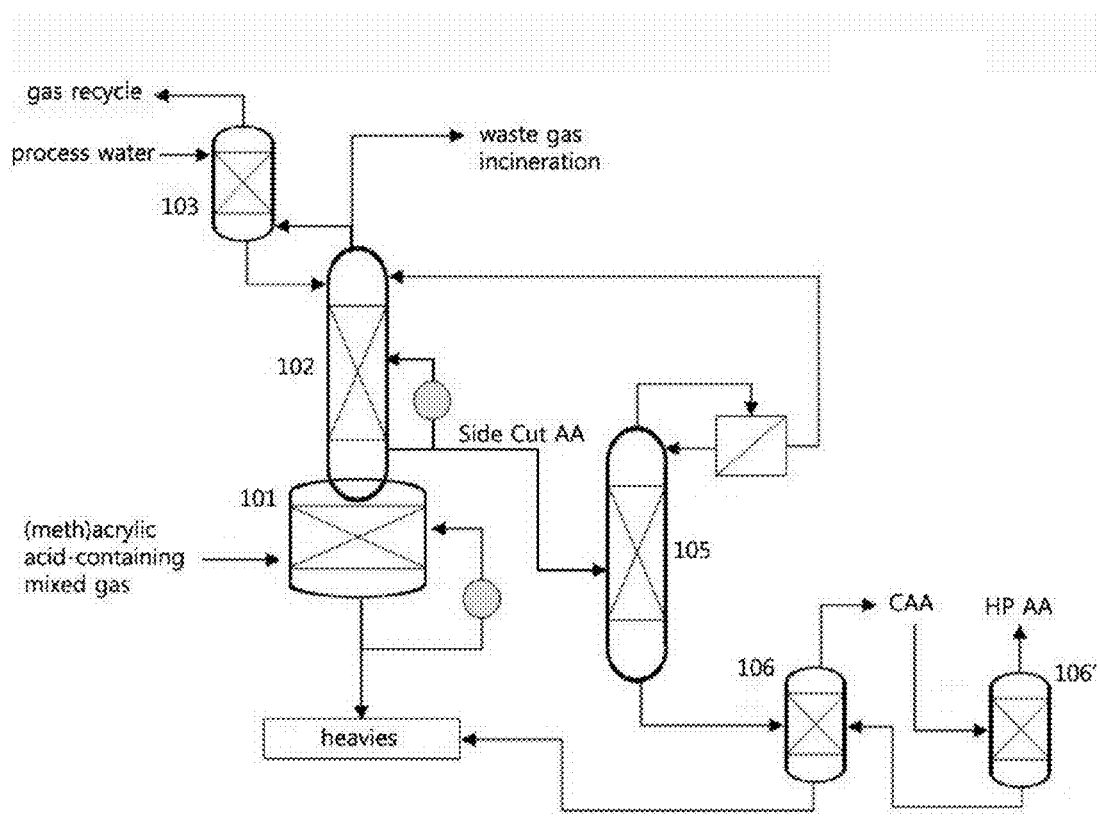

Meanwhile, FIG. 4 is a process diagram schematically showing the recovery method of (meth)acrylic acid according to another embodiment of the invention, wherein the method may be operated by the same process and conditions of FIG. 3, except that the quench tower (101) and the (meth)acrylic acid absorption tower (102) are integrated.

In the embodiment of FIG. 4, since the quench tower (101) and the (meth)acrylic acid absorption tower (102) are integrated, it is important to control the location of a side cut for recovering the (meth)acrylic acid aqueous solution in the (meth)acrylic acid absorption tower (102). According to one embodiment of the invention, the location of the side cut for recovering the (meth)acrylic acid aqueous solution may be selected from points where the temperature range of the integrated (meth)acrylic acid absorption tower (102) corresponds to the upper temperature range of the separated quench tower (102) as shown in FIG. 3.

As explained, the method of continuous recovery of (meth)acrylic acid according to the present invention includes: conducting gas phase oxidation of at least one compound selected from the group consisting of propane, propylene, butane, i-butylene, t-butylene, and (meth)acrolein in the presence of a catalyst to obtain a mixed gas containing (meth)acrylic acid; quenching the (meth)acrylic acid-containing mixed gas to remove high boiling point by-products in the (meth)acrylic acid-containing mixed gas; contacting the high boiling point by-product-free (meth)acrylic acid-containing mixed gas with water or an aqueous solution to obtain an aqueous solution containing (meth)acrylic acid; and purifying the (meth)acrylic acid-containing aqueous solution to obtain (meth)acrylic acid.

However, the method may further include steps commonly conducted in the art before or after each step, and the recovery method of the present invention is not limited to the above-explained steps.

According to another embodiment of the invention, an apparatus for continuous recovery of (meth)acrylic acid is provided, including:

a gas phase oxidation reactor (not shown) for conducting gas phase oxidation of at least one compound selected from the group consisting of propane, propylene, butane, i-butylene, t-butylene, and (meth)acrolein in the presence of a catalyst to prepare a mixed gas containing (meth)acrylic acid;

a quench tower (101) for quenching the (meth)acrylic acid-containing mixed gas supplied from the gas phase oxidation reactor to remove high boiling point by-products in the (meth)acrylic acid-containing mixed gas;

a (meth)acrylic acid absorption tower (102) for contacting the high boiling point by-product-free (meth)acrylic acid-containing mixed gas supplied from the quench tower (101)

with water or an aqueous solution to obtain an aqueous solution containing (meth)acrylic acid; and a distillation tower (105) for purifying the (meth)acrylic-containing aqueous solution supplied from the (meth)acrylic acid absorption tower (102) to obtain (meth)acrylic acid.

The quench tower (101) may be connected to and integrated with the bottom of the (meth)acrylic acid absorption tower (102).

The device may further include an acetic acid absorption tower (103) connected to the top of the (meth)acrylic acid absorption tower (102).

The device may further include a crystallizer (106) connected to the bottom of the distillation tower (105).

The distillation tower (105) may recycle the aqueous solution remaining after obtaining the (meth)acrylic acid to the (meth)acrylic acid absorption tower (102), and the recycled aqueous solution may contact high boiling point by-product-free (meth)acrylic acid-containing mixed gas.

Hereinafter, preferable examples are presented for complete understanding of the invention. However, these examples are only to illustrate the invention, and the scope of the invention is not limited thereto.

EXAMPLE 1

To investigate the energy reduction effect resulting from conducting the step of removing high boiling point by-products before passing a (meth)acrylic acid absorption tower in the continuous recovery process of (meth)acrylic acid according to the present invention, energy consumption amount required in a quench tower, a (meth)acrylic acid absorption tower, and an acetic acid absorption tower was measured using an ASPEN PLUS process simulator (Aspen-Tech Inc.).

First, as shown in FIG. 3, a simulator including a quench tower (101) for quenching the (meth)acrylic acid-containing mixed gas supplied from a gas phase oxidation reactor (not shown) to remove high boiling point by-products in the (meth)acrylic acid-containing mixed gas; a (meth)acrylic acid absorption tower (102) for contacting the high boiling point by-product-free (meth)acrylic acid-containing mixed gas supplied from the quench tower (101) with water or an aqueous solution to obtain an aqueous solution containing (meth)acrylic acid; an acetic acid absorption tower (103) connected to the top of the (meth)acrylic acid absorption tower (102); a distillation tower (105) for purifying the (meth)acrylic-containing aqueous solution supplied from the (meth)acrylic acid absorption tower (102) to obtain (meth)acrylic acid; and a crystallizer (106, 106') connected to the bottom of the distillation tower(105) was prepared.

The (meth)acrylic acid-containing mixed gas used for the simulation (i.e., mixed gas obtained through gas phase oxidation) included about 14.7 wt % of acrylic acid, about 0.2 wt % of acrolein, about 0.5 wt % of acetic acid, about 0.14 wt % of non-reacted propylene, about 3.1 wt % of carbon monoxide and carbon dioxide, about 9.4 wt % of water vapor, about 68.96 wt % of nitrogen and oxygen, and about 3 wt % of high boiling point by-products.

The temperature of the mixed gas was about 170° C., and it was introduced into the bottom of the quench tower (101) at a pressure of about 1.3 bar and at a flow of about 52,400 kg/h. This is a converted value based on the yearly acrylic acid production amount of about 60,000 tons.

At the bottom of the quench tower (101), a stream of mixed gas including about 50 wt % of acrylic acid, about 42 wt % of high boiling point by-products, and the remaining amount of other products was obtained at about 97° C., about 1.25 bar, and 400 kg/h, and all the high boiling point by-products included in the mixed gas were removed to the bottom of the quench tower (101).

Meanwhile, the upstream part of the quench tower (101) was communicated with the acrylic acid absorption tower (102), and at the bottom of the acrylic acid absorption tower (102), a stream of about 67 wt % acrylic acid aqueous solution was obtained at 11,200 kg/h.

Into the top of the acrylic acid absorption tower (102), about 4200 kg/h of an aqueous solution containing acrylic acid and acetic acid inflowed from a part of the upstream part of the distillation tower (105) was introduced together with the downstream part of the acetic acid absorption tower (103).

Further, about 35 wt % of the stream discharged to the top of the acrylic acid absorption tower (102) was passed through the acetic acid absorption tower (103; upper temperature of about 62° C.) and discharged at a pressure of about 1.12 bar, and recycled to the gas phase oxidation reactor (not shown). Process water (PW) was introduced at about 500 kg/h into the top of the acetic acid absorption tower (103), thus further absorbing acrylic acid and acetic acid, and thereby the downstream volume of the acetic acid absorption tower (103) was introduced into the top of the acrylic acid absorption tower (102). The stream passing through the acetic acid absorption tower (103) and recirculating to the gas phase oxidation reactor (not shown) was free of acrylic acid and acetic acid, and included about 13.3 wt % of moisture and the remaining part of non-condensable gasses (nitrogen, carbon dioxide, carbon monoxide, oxygen, non-reacted propylene, non-reacted propane, and the like).

Meanwhile, about 65 wt % of the stream discharged to the top of the acrylic acid absorption tower (102) was transferred to an incinerator (not shown) and discarded, and the stream included about 0.1 wt % of acrylic acid, about 0.1 wt % of acetic acid, about 0.2 wt % of acrolein, about 13.6 wt % of moisture, and the remaining part of non-condensable gasses (nitrogen, carbon dioxide, carbon monoxide, oxygen, non-reacted propylene, non-reacted propane, and the like).

As explained, the cooling energy consumed in the quench tower (101), acrylic acid absorption tower (102), and acetic acid absorption tower (103) was respectively about 0.565 Gcal/h at the quench tower, about 1.46 Gcal/h at the acrylic acid absorption tower, and about 0.03 Gcal/h at the acetic acid absorption tower, and the sum was about 2.055 Gcal/h.

The energy consumption amount is similar to the cooling energy of about 2 Gcal/h consumed in the acrylic acid absorption tower (102) in the existing process as shown in FIG. 1 or FIG. 2 (based on the yearly 60,000 tons of acrylic acid production amount).

EXAMPLE 2

A (meth)acrylic acid recovery process was simulated under the same conditions of FIG. 3, except using the apparatus shown in FIG. 4, wherein a quench tower (101) and a (meth)acrylic acid absorption tower (102) were integrated.

The (meth)acrylic acid-containing mixed gas of Example 1 was introduced into the bottom of a 7-stage absorption tower wherein a quench tower (101) and a (meth)acrylic acid absorption tower (102) were integrated (hereinafter referred to as acrylic acid absorption tower). The side cut of the acrylic acid absorption tower was made at the $5^{th}$ stage ('Side Cut AA' part), and cooling energy was introduced through cooling coils at the $4^{th}$ stage and $6^{th}$ stage.

At the bottom of the acrylic acid absorption tower, a stream of a mixture including about 44.2 wt % of acrylic acid, about 49.9 wt % of high boiling point by-products, and the remaining part of other products was obtained at about 102° C., 1.19 bar, and 335 kg/h, and all the high boiling point by-products included in the firstly introduced mixed gas were removed to the bottom of the acrylic acid absorption tower.

Meanwhile, at the $5^{th}$ side cut of the acrylic acid absorption tower, a stream of about 67 wt % acrylic acid aqueous solution having a temperature of 73.5° C. and pressure of 1.16 bar was obtained at 11,200 kg/g.

At the top of the acrylic acid absorption tower, about 4200 kg/h of an aqueous solution containing acrylic acid and acetic acid inflowed from a part of the upstream of the distillation tower (105) was introduced together with the downstream product of the acetic acid absorption tower (103).

About 35 wt % of the stream discharged to the top of the acrylic acid absorption tower was passed through an acetic acid absorption tower (103; upper temperature of about 62° C.) and discharged at a pressure of 1.12 bar, and recycled to a gas phase oxidation reactor (not shown). Herein, process water (PW) was introduced at about 500 kg/h into the top of the acetic acid absorption tower (103), thus further absorbing acrylic acid and acetic acid, and thereby the downstream product of the acetic acid absorption tower (103) was introduced into the top of the acrylic acid absorption tower (102). The stream passing through the acetic acid absorption tower (103) and recirculating to the gas phase oxidation reactor (not shown) was free of acrylic acid and acetic acid, and included about 13.4 wt % of moisture and the remaining part of non-condensable gasses (nitrogen, carbon dioxide, carbon monoxide, oxygen, non-reacted propylene, non-reacted propane, and the like).

Meanwhile, about 65 wt % of the stream discharged to the top of the acrylic acid absorption tower was transferred to an incinerator (not shown) and discarded, and the stream included about 0.2 wt % of acrylic acid, about 0.1 wt % of acetic acid, about 0.2 wt % of acrolein, about 13.7 wt % of moisture, and the remaining part of non-condensable gasses (nitrogen, carbon dioxide, carbon monoxide, oxygen, non-reacted propylene, non-reacted propane, and the like).

As explained, the cooling energy consumed in the process of FIG. 4 with the integrated quench tower was about 0.55 Gcal/h at the $6^{th}$ stage of the acrylic acid absorption tower, about 1.43 Gcal/h at the $4^{th}$ stage, and about 0.03 Gcal/h at the acetic acid absorption tower, and the sum was about 2.01 Gcal/h.

The energy consumption amount is similar to the cooling energy of about 2 Gcal/h consumed in the acrylic acid absorption tower (102) in the existing process as shown in FIG. 1 or FIG. 2 (based on yearly 60,000 tons of acrylic acid production amount).

As can be seen from Examples 1 and 2, the recovery method of (meth)acrylic acid according to the present invention may remove high boiling point by-products included in the mixed gas while operating an acrylic acid absorption tower, with similar energy to the energy consumed in the acrylic acid absorption tower (102) in the existing process as shown in FIG. 1 or FIG. 2 (about 2 Gcal/h), thus significantly reducing the energy consumption amount.

In addition, according to the existing process of FIG. 1 or FIG. 2, about 1.24 Gcal/h (base on the yearly 60,000 tons of acrylic acid production amount) of energy is additionally required for the operation of the high boiling point separation tower (108), which is an essential process after distillation of acrylic acid, but the method of the present invention may reduce energy cost corresponding thereto.

Description of Reference Numerals and Signs
- 101: quench tower
- 102: (meth)acrylic acid absorption tower
- 103: acetic acid absorption tower
- 105: distillation tower
- 106, 106': crystallizer
- 107: low boiling point separation tower
- 108: high boiling point separation tower
- 109: acetic acid separation tower
- 110: azeotropic solvent decanter

What is claimed:

1. An apparatus for continuous recovery of (meth)acrylic acid, comprising:
    a gas phase oxidation reactor for conducting gas phase oxidation of at least one compound selected from the group consisting of propane, propylene, butane, i-butylene, t-butylene, and (meth)acrolein in the presence of a catalyst to prepare a mixed gas containing (meth)acrylic acid;
    a quench tower for quenching the (meth)acrylic acid-containing mixed gas supplied from the gas phase oxidation reactor to remove high boiling point by-products in the (meth)acrylic acid-containing mixed gas;
    a (meth)acrylic acid absorption tower for contacting the high boiling point by-product-free (meth)acrylic acid-containing mixed gas with water or an aqueous solution to obtain an aqueous solution containing (meth)acrylic acid; and
    a distillation tower for purifying the (meth)acrylic-containing aqueous solution supplied from the (meth)acrylic acid absorption tower to obtain (meth)acrylic acid.

2. The apparatus for continuous recovery of (meth)acrylic acid according to claim 1, wherein the quench tower is connected to and integrated with the bottom of the (meth)acrylic acid absorption tower.

3. The apparatus for continuous recovery of (meth)acrylic acid according to claim 1, wherein the distillation tower recycles the aqueous solution remaining after obtaining the (meth)acrylic acid to the (meth)acrylic acid absorption tower, and the recycled aqueous solution contacts the high boiling point by-product-free (meth)acrylic acid-containing mixed gas.

4. The apparatus for continuous recovery of (meth)acrylic acid according to claim 1, wherein 5 to 80 wt % of the (meth)acrylic acid-containing aqueous solution discharged to the (meth)acrylic acid absorption tower is supplied to the quench tower, and the remainder is supplied in the distillation tower,
    the (meth)acrylic acid-containing mixed gas supplied to the quench tower is quenched by the (meth)acrylic acid-containing aqueous solution.

5. The apparatus for continuous recovery of (meth)acrylic acid according to claim 1, wherein the quenching the (meth)acrylic acid-containing mixed gas is conducted in the quench tower at a pressure of 1 to 1.5 bar and an upper temperature of 70 to 150° C.,
    the high boiling point by-products are discharged to the bottom of the quench tower, and the high boiling point by-product-free (meth)acrylic acid-containing mixed gas is discharged to the top of the quench tower.

6. The apparatus for continuous recovery of (meth)acrylic acid according to claim 1, wherein the contacting the high boiling point by-product-free (meth)acrylic acid-containing mixed gas is conducted in the absorption tower at a pressure of 1 to 1.5 bar and an upper temperature of 50 to 70° C.,
    the (meth)acrylic acid-containing aqueous solution is discharged to the bottom of the (meth)acrylic acid absorption tower, and a (meth)acrylic acid-stripped non-condensable gas is discharged to the top of the (meth)acrylic acid absorption tower.

7. The apparatus for continuous recovery of (meth)acrylic acid according to claim 1, wherein the purifying the (meth)acrylic acid-containing aqueous solution is conducted in the distillation tower supplied with a hydrophobic azeotropic solvent, discharged liquid including (meth)acrylic acid is recovered from the bottom of the distillation tower, and A discharged liquid including the azeotropic solvent, water, and acetic acid is recovered from the top of the distillation tower.

* * * * *